United States Patent
Hong et al.

(10) Patent No.: US 11,162,081 B2
(45) Date of Patent: Nov. 2, 2021

(54) KETOREDUCTASE MUTANT AND APPLICATION THEREOF

(71) Applicant: JILIN ASYMCHEM LABORATORIES CO., LTD., Jilin (CN)

(72) Inventors: Hao Hong, Morrisville, NC (US); Gage James, Morrisville, NC (US); Jiangping Lu, Tianjin (CN); Xingfu Xu, Tianjin (CN); Wenyan Yu, Tianjin (CN); Na Zhang, Tianjin (CN); Yulei Ma, Tianjin (CN); Yibing Cheng, Tianjin (CN); Huiyan Mu, Tianjin (CN)

(73) Assignee: JILIN ASYMCHEM LABORATORIES CO., LTD., Jilin (CN)

( * ) Notice: Subject to any disclaimer, the term of this patent is extended or adjusted under 35 U.S.C. 154(b) by 0 days.

(21) Appl. No.: 16/960,934

(22) PCT Filed: Jan. 22, 2018

(86) PCT No.: PCT/CN2018/073614
§ 371 (c)(1),
(2) Date: Jul. 9, 2020

(87) PCT Pub. No.: WO2019/140682
PCT Pub. Date: Jul. 25, 2019

(65) Prior Publication Data
US 2020/0354694 A1    Nov. 12, 2020

(51) Int. Cl.
| | | |
|---|---|---|
| C12N 9/04 | (2006.01) | |
| C12N 9/02 | (2006.01) | |
| C12P 17/00 | (2006.01) | |
| C12P 17/04 | (2006.01) | |
| C12P 21/00 | (2006.01) | |

(52) U.S. Cl.
CPC ............ *C12N 9/0006* (2013.01); *C12P 17/00* (2013.01); *C12P 17/04* (2013.01); *C12Y 101/01002* (2013.01)

(58) Field of Classification Search
CPC ........ C12N 15/70; C12N 9/00; C12N 9/0006; C12P 17/00; C12P 17/04; C12Y 101/01002

USPC .......... 435/189, 252.3, 320.1, 126, 130, 153
See application file for complete search history.

(56) References Cited

FOREIGN PATENT DOCUMENTS

| | | |
|---|---|---|
| CN | 107586793 A | 1/2016 |
| CN | 105624125 A | 6/2016 |
| WO | 2011005527 A2 | 1/2011 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
"Genbank accession No. WP_020944327.1," GENBANK, Aug. 6, 2013.
International Search Report for corresponding application PCT/CN2018/073614 filed Jan. 22, 2018; dated Oct. 25, 2018.
Database Uniprot [Online], Dec. 20, 2017, "SubName: Full=3-beta hydroxysteroid dyhydrogenase", XP002801679.
Database Uniprot [Online], Jun. 7, 2017, "SubName: Full=3-beta hydroxysteroid dyhydrogenase", XP0028001680.
European Search Report for corresponding application EP18901235; Report dated Jan. 18, 2021.

* cited by examiner

*Primary Examiner* — Robert B Mondesi
*Assistant Examiner* — Mohammad Y Meah
(74) *Attorney, Agent, or Firm* — Cantor Colburn LLP

(57) ABSTRACT

A ketoreductase mutant and use thereof are provided. The amino acid sequence of the ketoreductase mutant is an amino acid sequence obtained by mutation of the amino acid sequence shown in SEQ ID NO: 1, wherein the mutation at least comprises one of the following mutation sites: position 6, position 94, position 96, position 117, position 144, position 156, position 193, position 205, position 224, position 176, position 85 and position 108; alternatively, the amino acid sequence of the ketoreductase mutant has a mutation site in a mutated amino acid sequence and an amino acid sequence having 80% or more homology with the mutated amino acid sequence.

14 Claims, 1 Drawing Sheet
Specification includes a Sequence Listing.

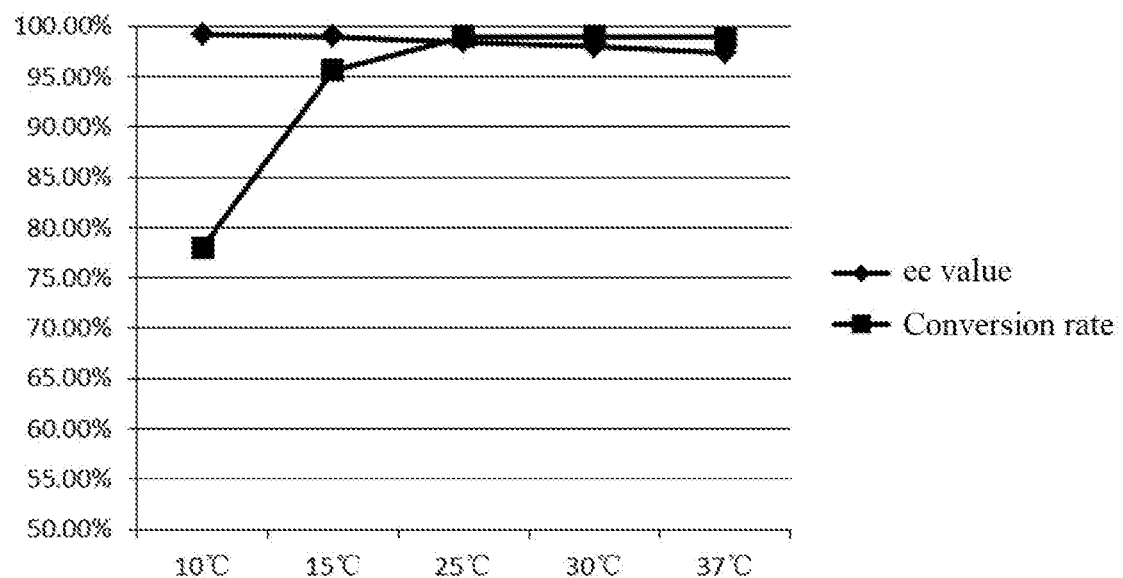

SEQUENCE LISTING

<160> NUMBER OF SEQ ID NOS: 43

<210> SEQ ID NO 1
<211> LENGTH: 253
<212> TYPE: PRT
<213> ORGANISM: Acetobacter pasteurianus 386B

<400> SEQUENCE: 1

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
    130                 135                 140
```

```
Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 2
<211> LENGTH: 253
<212> TYPE: PRT
<213> ORGANISM: Acetobacter pasteurianus 386B

<400> SEQUENCE: 2

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
    130                 135                 140

Gly Leu Ile Gly Asp Pro Met Leu Ala Ala Tyr Ser Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 3
<211> LENGTH: 253
<212> TYPE: PRT
<213> ORGANISM: Acetobacter pasteurianus 386B

<400> SEQUENCE: 3

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Pro
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 4
<211> LENGTH: 253
<212> TYPE: PRT
<213> ORGANISM: Acetobacter pasteurianus 386B

<400> SEQUENCE: 4

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
            85                  90                  95

Gly Ser Val Glu Ser Thr Ser Leu Glu Asp Trp Arg Val Gln Ser
        100                 105                 110

Ile Asn Leu Asp Ser Val Phe Leu Gly Thr Gln Val Ala Ile Glu Ala
            115                 120                 125

Met Lys Lys Ser Gly Gly Ser Ile Val Asn Leu Ser Ser Ile Glu
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 5
<211> LENGTH: 253
<212> TYPE: PRT
<213> ORGANISM: Acetobacter pasteurianus 386B

<400> SEQUENCE: 5

Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
            85                  90                  95

Gly Ser Val Glu Ser Thr Ser Leu Glu Asp Trp Arg Val Gln Ser
        100                 105                 110

Ile Asn Leu Asp Gly Val Phe Leu Gly Thr Gln Val Ala Ile Glu Ala
            115                 120                 125

Met Lys Lys Ser Gly Gly Ser Ile Val Asn Leu Ser Ser Ile Glu
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

```
Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250

<210> SEQ ID NO 6
<211> LENGTH: 253
<212> TYPE: PRT
<213> ORGANISM: Acetobacter pasteurianus 386B

<400> SEQUENCE: 6

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250

<210> SEQ ID NO 7
<211> LENGTH: 253
<212> TYPE: PRT
<213> ORGANISM: Acetobacter pasteurianus 386B

<400> SEQUENCE: 7

Met Ala Arg Val Ala Gly Lys Val Ala Ile Val Ser Gly Ala Ala Asn
1               5                   10                  15
```

```
Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Ser Ile Val Asn Leu Ser Ser Ile Glu
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 8
<211> LENGTH: 253
<212> TYPE: PRT
<213> ORGANISM: Acetobacter pasteurianus 386B

<400> SEQUENCE: 8

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ser Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125
```

```
Met Lys Lys Ser Gly Gly Gly Ser Ile Val Asn Leu Ser Ser Ile Glu
            130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Pro Met Val Ala Gly Leu Thr Lys Glu Asp Ala Ala Arg Gln Lys
                195                 200                 205

Leu Val Asp Leu His Pro Ile Gly His Leu Gly Glu Pro Asn Asp Ile
            210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 9
<211> LENGTH: 253
<212> TYPE: PRT
<213> ORGANISM: Acetobacter pasteurianus 386B

<400> SEQUENCE: 9

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Asp Gly Gln Lys Ala Val Ala
            35                  40                  45

Glu Ile Lys Ala Ala Gly Gly Glu Ala Ala Phe Val Lys Leu Asn Val
        50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
            130                 135                 140

Gly Leu Ile Gly Asp Pro Met Leu Ala Ala Tyr Cys Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Pro Met Val Ala Gly Leu Thr Lys Glu Asp Ala Ala Arg Gln Lys
                195                 200                 205

Leu Val Asp Leu His Pro Ile Gly His Leu Gly Glu Pro Asn Asp Ile
            210                 215                 220

Ala Tyr Gly Ile Leu Tyr Leu Ala Ser Asp Glu Ser Lys Phe Val Thr
225                 230                 235                 240
```

Gly Ser Glu Leu Val Ile Asp Gly Gly Tyr Thr Ala Gln
            245                 250

<210> SEQ ID NO 10
<211> LENGTH: 253
<212> TYPE: PRT
<213> ORGANISM: Acetobacter pasteurianus 386B

<400> SEQUENCE: 10

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
    130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250

<210> SEQ ID NO 11
<211> LENGTH: 253
<212> TYPE: PRT
<213> ORGANISM: Acetobacter pasteurianus 386B

<400> SEQUENCE: 11

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

```
Thr Asp Glu Ala Ala Trp Lys Ala Ala Ile Gly Gln Thr Leu Lys Leu
 65                  70                  75                  80

Tyr Gly Arg Leu Asp Ile Ala Val Asn Asn Ala Gly Ile Ala Tyr Ser
                 85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Gly Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 12
<211> LENGTH: 253
<212> TYPE: PRT
<213> ORGANISM: Acetobacter pasteurianus 386B

<400> SEQUENCE: 12

Met Ala Arg Val Ala Gly Lys Val Ala Ile Val Ser Gly Ala Ala Asn
 1               5                  10                  15

Gly Ile Gly Lys Ala Thr Ala Gln Leu Leu Ala Lys Glu Gly Ala Lys
                 20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
        50                  55                  60

Thr Asp Glu Ala Ala Trp Lys Ala Ala Ile Gly Gln Thr Leu Lys Leu
 65                  70                  75                  80

Tyr Gly Arg Leu Asp Ile Ala Val Asn Asn Ala Gly Ile Ala Tyr Ser
                 85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175
```

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Gln Arg Gln Lys
            195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250

<210> SEQ ID NO 13
<211> LENGTH: 253
<212> TYPE: PRT
<213> ORGANISM: Acetobacter pasteurianus 386B

<400> SEQUENCE: 13

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Ser Ile Val Asn Leu Ser Ser Ile Glu
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
            195                 200                 205

Leu Val Asp Leu His Pro Ile Gly His Leu Gly Glu Pro Asn Asp Val
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250

<210> SEQ ID NO 14
<211> LENGTH: 253
<212> TYPE: PRT
<213> ORGANISM: Acetobacter pasteurianus 386B

<400> SEQUENCE: 14

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Glu
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Pro
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 15
<211> LENGTH: 253
<212> TYPE: PRT
<213> ORGANISM: Acetobacter pasteurianus 386B

<400> SEQUENCE: 15

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Glu Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110
```

```
Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Glu
        130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 16
<211> LENGTH: 253
<212> TYPE: PRT
<213> ORGANISM: Acetobacter pasteurianus 386B

<400> SEQUENCE: 16

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp His Arg Val Gln Ser
            100                 105                 110

Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Glu
        130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220
```

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 17
<211> LENGTH: 253
<212> TYPE: PRT
<213> ORGANISM: Acetobacter pasteurianus 386B

<400> SEQUENCE: 17

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Pro
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 18
<211> LENGTH: 253
<212> TYPE: PRT
<213> ORGANISM: Acetobacter pasteurianus 386B

<400> SEQUENCE: 18

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
            50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ser Tyr Ser
                    85                  90                  95

Gly Ser Val Glu Ser Thr Ser Leu Glu Asp Trp Arg Arg Val Gln Ser
                100                 105                 110

Ile Asn Leu Asp Gly Val Phe Leu Gly Thr Gln Val Ala Ile Glu Ala
            115                 120                 125

Met Lys Lys Ser Gly Gly Ser Ile Val Asn Leu Ser Ser Ile Ser
            130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Pro Met Val Ala Gly Leu Thr Lys Glu Asp Ala Ala Arg Gln Lys
            195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 19
<211> LENGTH: 253
<212> TYPE: PRT
<213> ORGANISM: Acetobacter pasteurianus 386B

<400> SEQUENCE: 19

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
            50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Ser
                    85                  90                  95

Gly Ser Val Glu Ser Thr Ser Leu Glu Asp Trp Arg Arg Val Gln Ser
                100                 105                 110

Ile Asn Leu Asp Gly Val Phe Leu Gly Thr Gln Val Ala Ile Glu Ala
            115                 120                 125

Met Lys Lys Ser Gly Gly Ser Ile Val Asn Leu Ser Ser Ile Ser
            130                 135                 140

Gly Leu Ile Gly Asp Pro Met Leu Ala Ala Tyr Asn Ala Ser Lys Gly
145                 150                 155                 160

```
Gly Val Arg Leu Phe Thr Lys Ser Ala Ala Leu His Cys Ala Lys Ser
            165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
            195                 200             205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250
```

<210> SEQ ID NO 20
<211> LENGTH: 253
<212> TYPE: PRT
<213> ORGANISM: Acetobacter pasteurianus 386B

<400> SEQUENCE: 20

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Asp Gly Gln Lys Ala Val Ala
            35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
            85                  90                  95

Gly Ser Val Glu Ser Thr Ser Leu Glu Asp Trp Arg Arg Val Gln Ser
            100                 105                 110

Ile Asn Leu Asp Ser Val Phe Leu Gly Thr Gln Val Ala Ile Glu Ala
            115                 120                 125

Met Lys Lys Ser Gly Gly Gly Ser Ile Val Asn Leu Ser Ser Ile Ser
            130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
            165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
            195                 200             205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250
```

<210> SEQ ID NO 21
<211> LENGTH: 253
<212> TYPE: PRT

<213> ORGANISM: Acetobacter pasteurianus 386B

<400> SEQUENCE: 21

| Met | Ala | Arg | Val | Ala | Ser | Lys | Val | Ala | Ile | Val | Ser | Gly | Ala | Ala | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 22
<211> LENGTH: 253
<212> TYPE: PRT
<213> ORGANISM: Acetobacter pasteurianus 386B

<400> SEQUENCE: 22

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Ser
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Gln Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 23
<211> LENGTH: 253
<212> TYPE: PRT
<213> ORGANISM: Acetobacter pasteurianus 386B

<400> SEQUENCE: 23

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Ser
        130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

```
Leu Val Asp Leu His Pro Ile Gly His Leu Gly Glu Pro Asn Asp Val
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 24
<211> LENGTH: 253
<212> TYPE: PRT
<213> ORGANISM: Acetobacter pasteurianus 386B

<400> SEQUENCE: 24

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
        50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Pro
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 25
<211> LENGTH: 253
<212> TYPE: PRT
<213> ORGANISM: Acetobacter pasteurianus 386B

<400> SEQUENCE: 25

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30
```

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
         50                  55                  60

Thr Asp Glu Ala Ala Trp Lys Ala Ala Ile Gly Gln Thr Leu Lys Leu
 65                  70                  75                  80

Tyr Gly Arg Leu Asp Ile Ala Val Asn Asn Ala Gly Ile Ala Tyr Ser
                 85                  90                  95

Gly Ser Val Glu Ser Thr Ser Leu Glu Asp Trp Arg Val Gln Ser
                100                 105                 110

Ile Asn Leu Asp Gly Val Phe Leu Gly Thr Gln Val Ala Ile Glu Ala
             115                 120                 125

Met Lys Lys Ser Gly Gly Gly Ser Ile Val Asn Leu Ser Ser Ile Ser
130                 135                 140

Gly Leu Ile Gly Asp Pro Met Leu Ala Ala Tyr Cys Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
            195                 200                 205

Leu Val Asp Leu His Pro Ile Gly His Leu Gly Glu Pro Asn Asp Ile
        210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 26
<211> LENGTH: 253
<212> TYPE: PRT
<213> ORGANISM: Acetobacter pasteurianus 386B

<400> SEQUENCE: 26

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
         50                  55                  60

Thr Asp Glu Ala Ala Trp Lys Ala Ala Ile Gly Gln Thr Leu Lys Leu
 65                  70                  75                  80

Tyr Gly Arg Leu Asp Ile Ala Val Asn Asn Ala Gly Ile Ser Tyr Pro
                 85                  90                  95

Gly Ser Val Glu Ser Thr Ser Leu Glu Asp Trp Arg Val Gln Ser
                100                 105                 110

Ile Asn Leu Asp Gly Val Phe Leu Gly Thr Gln Val Ala Ile Glu Ala
             115                 120                 125

Met Lys Lys Ser Gly Gly Gly Ser Ile Val Asn Leu Ser Ser Ile Ser
130                 135                 140

```
Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 27
<211> LENGTH: 253
<212> TYPE: PRT
<213> ORGANISM: Acetobacter pasteurianus 386B

<400> SEQUENCE: 27

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Glu Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Ser Ile Val Asn Leu Ser Ser Ile Ser
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

```
<210> SEQ ID NO 28
<211> LENGTH: 253
<212> TYPE: PRT
<213> ORGANISM: Acetobacter pasteurianus 386B

<400> SEQUENCE: 28

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp His Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 29
<211> LENGTH: 253
<212> TYPE: PRT
<213> ORGANISM: Acetobacter pasteurianus 386B

<400> SEQUENCE: 29

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80
```

```
Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
            115                 120                 125

Met Lys Lys Ser Gly Gly Ser Ile Val Asn Leu Ser Ser Ile Ser
    130                 135                 140

Gly Leu Ile Gly Asp Pro Met Leu Ala Ala Tyr Ser Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
            195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 30
<211> LENGTH: 253
<212> TYPE: PRT
<213> ORGANISM: Acetobacter pasteurianus 386B

<400> SEQUENCE: 30

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
            115                 120                 125

Met Lys Lys Ser Gly Gly Ser Ile Val Asn Leu Ser Ser Ile Ser
    130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190
```

```
Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 31
<211> LENGTH: 253
<212> TYPE: PRT
<213> ORGANISM: Acetobacter pasteurianus 386B

<400> SEQUENCE: 31

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Gly Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 32
<211> LENGTH: 253
<212> TYPE: PRT
<213> ORGANISM: Acetobacter pasteurianus 386B

<400> SEQUENCE: 32

Met Ala Arg Val Ala Gly Lys Val Ala Ile Val Ser Gly Ala Ala Asn
1               5                   10                  15
```

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Ser Ile Val Asn Leu Ser Ser Ile Ser
    130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 33
<211> LENGTH: 253
<212> TYPE: PRT
<213> ORGANISM: Acetobacter pasteurianus 386B

<400> SEQUENCE: 33

Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ser Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

```
Met Lys Lys Ser Gly Gly Gly Ser Ile Val Asn Leu Ser Ser Ile Ser
        130                 135                 140

Gly Leu Ile Gly Asp Pro Met Leu Ala Ala Tyr Asn Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Pro Met Val Ala Gly Leu Thr Lys Glu Asp Ala Ala Arg Gln Lys
                195                 200                 205

Leu Val Asp Leu His Pro Ile Gly His Leu Gly Glu Pro Asn Asp Ile
        210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 34
<211> LENGTH: 253
<212> TYPE: PRT
<213> ORGANISM: Acetobacter pasteurianus 386B

<400> SEQUENCE: 34

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Asp Gly Gln Lys Ala Val Ala
        35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Met Tyr Ser
                85                  90                  95

Gly Ser Val Glu Ser Thr Ser Leu Glu Asp Trp Arg Arg Val Gln Ser
                100                 105                 110

Ile Asn Leu Asp Gly Val Phe Leu Gly Thr Gln Val Ala Ile Glu Ala
                115                 120                 125

Met Lys Lys Ser Gly Gly Gly Ser Ile Val Asn Leu Ser Ser Ile Ser
        130                 135                 140

Gly Leu Ile Gly Asp Pro Met Leu Ala Ala Tyr Phe Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Pro Met Val Ala Gly Leu Thr Lys Glu Asp Ala Ala Arg Gln Lys
                195                 200                 205

Leu Val Asp Leu His Pro Ile Gly His Leu Gly Glu Pro Asn Asp Ile
        210                 215                 220

Ala Tyr Gly Ile Leu Tyr Leu Ala Ser Asp Glu Ser Lys Phe Val Thr
225                 230                 235                 240
```

```
Gly Ser Glu Leu Val Ile Asp Gly Gly Tyr Thr Ala Gln
            245                 250
```

<210> SEQ ID NO 35
<211> LENGTH: 253
<212> TYPE: PRT
<213> ORGANISM: Acetobacter pasteurianus 386B

<400> SEQUENCE: 35

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Asn Tyr Ser
                85                  90                  95

Gly Ser Val Glu Ser Thr Ser Leu Glu Asp Trp Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Val Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250
```

<210> SEQ ID NO 36
<211> LENGTH: 253
<212> TYPE: PRT
<213> ORGANISM: Acetobacter pasteurianus 386B

<400> SEQUENCE: 36

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60
```

```
Thr Asp Glu Ala Ala Trp Lys Ala Ala Ile Gly Gln Thr Leu Lys Leu
 65                  70                  75                  80

Tyr Gly Arg Leu Asp Ile Ala Val Asn Asn Ala Gly Ile Asn Tyr Ser
                 85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Gly Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 37
<211> LENGTH: 253
<212> TYPE: PRT
<213> ORGANISM: Acetobacter pasteurianus 386B

<400> SEQUENCE: 37

Met Ala Arg Val Ala Gly Lys Val Ala Ile Val Ser Gly Ala Ala Asn
 1                5                  10                  15

Gly Ile Gly Lys Ala Thr Ala Gln Leu Leu Ala Lys Glu Gly Ala Lys
             20                  25                  30

Val Val Ile Gly Asp Leu Lys Glu Glu Asp Gly Gln Lys Ala Val Ala
         35                  40                  45

Glu Ile Lys Ala Ala Gly Gly Glu Ala Ala Phe Val Lys Leu Asn Val
     50                  55                  60

Thr Asp Glu Ala Ala Trp Lys Ala Ala Ile Gly Gln Thr Leu Lys Leu
 65                  70                  75                  80

Tyr Gly Arg Leu Asp Ile Ala Val Asn Asn Ala Gly Ile Pro Tyr Ser
                 85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175
```

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
            195                 200                 205

Leu Val Asp Leu His Pro Ile Gly His Leu Gly Glu Pro Asn Asp Ile
        210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 38
<211> LENGTH: 253
<212> TYPE: PRT
<213> ORGANISM: Acetobacter pasteurianus 386B

<400> SEQUENCE: 38

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Arg Tyr Ser
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Cys Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
            195                 200                 205

Leu Val Asp Leu His Pro Ile Gly His Leu Gly Glu Pro Asn Asp Ile
        210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 39
<211> LENGTH: 253
<212> TYPE: PRT
<213> ORGANISM: Acetobacter pasteurianus 386

<400> SEQUENCE: 39

```
Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Ser
                85                  90                  95

Gly Ser Val Glu Ser Thr Ser Leu Glu Asp Trp Arg Arg Val Gln Ser
                100                 105                 110

Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Ser
130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Pro Met Val Ala Gly Leu Thr Lys Glu Asp Ala Ala Ala Arg Gln Lys
            195                 200                 205

Leu Val Asp Leu His Pro Ile Gly His Leu Gly Glu Pro Asn Asp Ile
210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 40
<211> LENGTH: 253
<212> TYPE: PRT
<213> ORGANISM: Acetobacter pasteurianus 386B

<400> SEQUENCE: 40

```
Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Asn Tyr Pro
                85                  90                  95

Gly Ser Val Glu Ser Thr Ser Leu Glu Asp Trp Arg Arg Val Gln Ser
                100                 105                 110
```

```
Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Ser
        130                 135                 140

Gly Leu Ile Gly Asp Pro Met Leu Ala Ala Tyr Val Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250

<210> SEQ ID NO 41
<211> LENGTH: 253
<212> TYPE: PRT
<213> ORGANISM: Acetobacter pasteurianus 386B

<400> SEQUENCE: 41

Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
            20                  25                  30

Val Val Ile Gly Asp Leu Lys Glu Glu Asp Gly Gln Lys Ala Val Ala
        35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Pro
                85                  90                  95

Gly Ser Val Glu Ser Thr Ser Leu Glu Asp Trp Arg Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Arg Gln Lys
        195                 200                 205

Leu Val Asp Leu His Pro Ile Gly His Leu Gly Glu Pro Asn Asp Ile
    210                 215                 220
```

-continued

```
Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 42
<211> LENGTH: 253
<212> TYPE: PRT
<213> ORGANISM: Acetobacter pasteurianus 386B

<400> SEQUENCE: 42

```
Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Glu Asp Gly Gln Lys Ala Val Ala
            35                  40                  45

Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Thr Tyr Pro
                85                  90                  95

Gly Ser Val Glu Ser Thr Ser Leu Glu Asp Trp His Arg Val Gln Ser
            100                 105                 110

Ile Asn Leu Asp Gly Val Phe Leu Gly Thr Gln Val Ala Ile Glu Ala
        115                 120                 125

Met Lys Lys Ser Gly Gly Gly Ser Ile Val Asn Leu Ser Ser Ile Ser
130                 135                 140

Gly Leu Ile Gly Asp Pro Met Leu Ala Ala Tyr Thr Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
            180                 185                 190

Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

<210> SEQ ID NO 43
<211> LENGTH: 253
<212> TYPE: PRT
<213> ORGANISM: Acetobacter pasteurianus 386B

<400> SEQUENCE: 43

```
Met Ala Arg Val Ala Ser Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Glu Asp Gly Gln Lys Ala Val Ala
            35                  40                  45
```

```
Glu Ile Lys Ala Ala Gly Gly Glu Ala Ala Phe Val Lys Leu Asn Val
    50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Asn Tyr Pro
                85                  90                  95

Gly Ser Val Glu Ser Thr Ser Leu Glu Asp Trp His Arg Val Gln Ser
            100                 105                 110

Ile Asn Leu Asp Gly Val Phe Leu Gly Thr Gln Val Ala Ile Glu Ala
            115                 120                 125

Met Lys Lys Ser Gly Gly Gly Ser Ile Val Asn Leu Ser Ser Ile Ser
    130                 135                 140

Gly Leu Ile Gly Asp Pro Met Leu Ala Ala Tyr Val Ala Ser Lys Gly
145                 150                 155                 160

Gly Val Arg Leu Phe Thr Lys Ser Ala Ala Leu His Cys Ala Lys Ser
                165                 170                 175

Gly Tyr Lys Ile Arg Val Asn Ser Val His Pro Gly Tyr Ile Trp Thr
                180                 185                 190

Gly Met Val Ala Gly Leu Thr Lys Glu Asp Ala Ala Ala Arg Gln Lys
            195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
            245                 250
```

KETOREDUCTASE MUTANT AND APPLICATION THEREOF

INCORPORATION BY REFERENCE

In compliance with 37 C.F.R. § 1.52(e)(5), M.P.E.P.§ 608.05(I), the sequence information contained in electronic file named: Sequence Listing.txt; size 2.43 kilobytes; created on Jul. 8, 2020 using PatentIn 3.5.1 is hereby incorporated by reference in its entirety.

TECHNICAL FIELD

The disclosure relates to the field of biotechnology, in particular to a ketoreductase mutant and use thereof.

BACKGROUND

Chiral alcohols are a class of optically active compounds with hydroxyl groups on chiral carbons, which are widely used in the synthesis of chiral drugs and other chiral fine chemicals. The traditional chemical synthesis method has the problems of serious environmental pollution, low product purity, harsh catalytic conditions or expensive catalyst and the like. Ketoreductase is widely used in the synthesis of optically active alcohols due to its high efficiency, high stereoselectivity, mild conditions, being environmentally friendly and many other advantages.

Ketoreductase, also known as carbonyl reductase or alcohol dehydrogenase, is a ubiquitous oxidoreductase in nature that will reversibly catalyze the reduction of ketones or aldehydes to alcohols. Ketoreductase catalyzes the reduction of ketones requiring the transfer of hydrogen to the carbonyl by cofactors, the commonly used cofactors are reduced nicotinamide adenine dinucleotide phosphate (NADPH) or reduced nicotinamide adenine dinucleotide (NADH).

Ketoreductase from microbial cells or microorganisms can efficiently catalyze the reduction of prochiral ketones, and is one of the important methods for preparing chiral alcohol molecules. However, when natural enzymes catalyze non-natural substrates, their reaction selectivity, catalytic activity and stability are not ideal and cannot meet the requirements of industrial applications. The modification of wild enzymes by means of protein engineering is an effective means to improve the enzymatic properties of non-natural substrates.

R-3-hydroxy heterocyclic compounds, such as R-3-hydroxytetrahydrofuran and R-3-hydroxytetrahydrothiophene, are important pharmaceutical intermediates. (R)-3-hydroxytetrahydrothiophene, which is a key intermediate in the production of various drugs such as antibiotics and protease inhibitors, especially the antibiotic sulopenem, and the production of salts or solvates and hydrates thereof. It has been reported that (R)-3-hydroxytetrahydrothiophene is prepared from L-aspartic acid by a five-step chemical reaction, which causes serious environmental pollution.

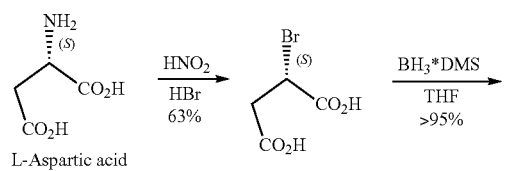
L-Aspartic acid

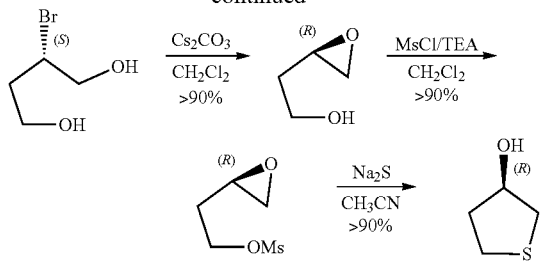

Compared with a chemical synthesis method, the biocatalysis method is greener and environment-friendly. However, the existing wild-type enzyme is low in selectivity and poor in stability, resulting in complex reaction system, complicated post-reaction treatment process and high production costs.

SUMMARY

The disclosure aims to provide a ketoreductase mutant and use thereof, so as to solve the technical problems of low selectivity and poor stability of a wild-type enzyme in the prior art.

To achieve the above object, according to one aspect of the present disclosure, a ketoreductase mutant is provided. The amino acid sequence of the ketoreductase mutant is an amino acid sequence has more than 80% homology with the amino acid sequence shown in SEQ ID NO: 1, wherein the mutation at least contains one of the following mutation sites: positions 6, 94, 96, 117, 144, 156, 193, 205, 224, 176, 85 and 108, and glycine at position 6 is mutated to serine; alanine at position 94 is mutated to serine or threonine; serine at position 96 is mutated to proline, asparagine, arginine or methionine; glycine at position 117 is mutated to serine; glutamic acid at position 144 is mutated to serine, asparagine at position 156 is mutated to threonine, cysteine, serine, valine, glycine or phenylalanine, proline at position 193 is mutated to glycine, alanine at position 205 is mutated to glutamine, isoleucine at position 224 is mutated to valine, serine at position 96 is mutated to proline and serine at position 176 is mutated to proline, aspartic acid at position 85 is mutated to glutamic acid and arginine at position 108 is mutated to histidine.

Furthermore, the ketoreductase mutant has more than 95%, preferably 96%, more preferably 97%, 98%, 99% or 100% of homology with the amino acid sequences shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43.

According to another aspect of the present disclosure, a DNA molecule is provided. The DNA molecule encodes any one of the ketoreductase mutants described above.

Further, the sequence of the DNA molecule has more than 95%, preferably 96% homology, and preferably a sequence of 97%, 98%, 99% or 100% homology with the sequence shown in SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85 or SEQ ID NO: 86.

According to a further aspect of the present disclosure, a recombinant plasmid containing any of the DNA molecules described above is provided.

Further, the recombinant plasmid is pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to yet another aspect of the present disclosure, a host cell is provided. The host cell contains any of the recombinant plasmids described above.

Further, the host cell contains a prokaryotic cell, a yeast or a eukaryotic cell; preferably, the prokaryotic cell is an *Escherichia coli* (*E. coli*) BL21 cell or an *E. coli* DH5α competent cell.

According to yet another aspect of the present disclosure, a method for producing an R-3-hydroxy heterocyclic compound is provided. The method contains the steps of catalytic reduction of a ketone compound by ketone reductase, wherein the ketone reductase is the mutant of ketone reductase.

Further, the ketone compound is

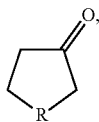

and the product of the reduction reaction is

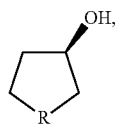

wherein R is selected from O or S atom.

Further, conversion rate of R-3-hydroxytetrahydrofuran is >99% with an ee value is 99.6%; conversion rate of R-3-hydroxytetrahydrothiophene is >99% with an ee of 99.8%.

Further, the ketoreductase is a solution, lyophilized powder, immobilized enzyme or immobilized cell of the above ketoreductase mutant.

Furthermore, the reaction system of catalytic reduction reaction also includes cofactors, which are isopropanol and no other coenzyme are added.

Further, the reaction system of the catalytic reduction reaction includes cofactors such as NAD/NADH and/or NADP/NADPH, cofactor circulatory system including glucose and glucose dehydrogenase, formate and formate dehydrogenase, glucose 6-phosphate and glucose-6-phosphate dehydrogenase, or secondary alcohol and secondary alcohol dehydrogenase.

Furthermore, the amount of ketoreductase in the catalytic reduction reaction system is 5 mg~0.1 g crude enzyme lyophilized powder/1 g substrate.

Further, the temperature of the catalytic reduction reaction is 10~37° C., preferably 15~35° C.

Further, the catalytic reduction reaction time is 3~48 h, more preferably 6~27 h.

Further, the catalytic reduction reaction is carried out under a condition of pH of 6.0-9.5, preferably the pH is 7.0~7.5.

The disclosure evolves the wild ketoreductase acCR by means of protein engineering, and obtains the engineered ketoreductase with highly improved enzymatic performance, and the stability of these ketoreductase mutants is significantly improved, especially for acetone and isopropanol, so that in the preparation of chiral hydroxyl heterocyclic substances, there is not need to add glucose/glucose dehydrogenase and formate/formate dehydrogenase, or other coenzymes, the regeneration of cofactors can be completed by adding only isopropanol, which simplifies the composition of the reaction system and reduces the cost. In addition, the ketoreductase mutant disclosed by the disclosure has high stereoselectivity, can be used for preparing chiral alcohol with nearly single purity, so that the utilization rate of a substrate is increased, the post-treatment steps are reduced, and the application value of industrial production of the ketoreductase mutant is improved.

BRIEF DESCRIPTION OF THE DRAWINGS

The drawings, which constitute a part of this application, are used to provide a further understanding of the present disclosure. The illustrative embodiments of the present disclosure and the descriptions thereof are used to explain the present disclosure, and do not constitute an improper limitation on the present disclosure. In the drawings:

FIG. 1 shows the conversion results in the optimization of the reaction temperature in Example 6.

DETAILED DESCRIPTION OF THE EMBODIMENTS

It should be noted that the examples and features in the examples herein may be combined with one another without conflict. The present disclosure will be described in detail below with reference to the drawings and in conjunction with the embodiments.

Wild-type ketoreductase acCR from *Acetobacter pasteurianus* 386B catalyzes the conversion of substrate I to product II, but its selectivity is poor and the ee value of the resulting R-3-hydroxy heterocyclic compound is only 54%. The disclosure aims to improve the stereoselectivity and/or stability of the ketoreductase acCR by a protein engineering method, obtains a mutant with improved enzyme catalytic characteristics, and obtain chiral alcohol with high optical purity in the production and preparation process of chiral compounds.

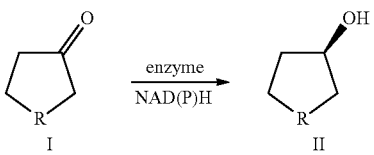

R is selected from an "O" or "S" atom.

In protein engineering, site-directed mutagenesis and saturation mutagenesis are effective methods to modify enzyme molecules. Firstly, a mutation site was introduced on acCR by a full-plasmid PCR mode, and selecting a mutant with improved selectivity or stability by a directional screening method for the mutant.

35 pairs of site-directed mutagenesis primers (G6S, L38S, K71R, D85E, A94T, A94G, S96P, S101A, L104A, R108H, V110L, Q111T, G117S, V118I, T122A, M129I, I143L, E144S, L146A, I147V, D149I, P150I, N156T, N156S, N156C, R163K, K167A, S176P, V185I, P193N, P193G, A196E, A203D, A205Q, I224V) were designed by using acCR as template, using site-directed mutagenesis, the mutant plasmid with target gene was obtained by using pET-22b(+) as expression vector.

Wherein, site-directed mutagenesis: refers to the introduction of desired changes (usually characterizing changes in favorable directions) to the target DNA fragments (either genomes or plasmids) by polymerase chain reaction (PCR), including addition, deletion, point mutation, etc. of bases. Site-directed mutagenesis can rapidly and efficiently improve the properties and characterization of target proteins expressed by DNA, and is a very useful means in gene research.

The method of introducing site-directed mutation by whole plasmid PCR is simple and effective, and is a widely used method at present. The principle is as follows, a pair of primers containing mutation sites (forward and reverse), and the template plasmid is annealed, then "cycled extended" by polymerase, the so-called cyclic extension means that the polymerase extends the primers according to the template, and then returns to the 5' end of the primers after a circle, after cycles of repeated heating and annealing, this reaction is different from rolling circle amplification, will not form multiple tandem copies. The extension products of the forward primer and the reverse primer are annealed and paired to form a nicked open circular plasmid. Dpn I digests the extension product, since the original template plasmid is derived from conventional E. coli, subjected to dam methylation modification and sensitive to Dpn I, it is chopped, and the plasmid with the mutant sequence synthesized in vitro is not cut due to no methylation, so that the plasmid is successfully transformed in subsequent transformation, and clone of the mutant plasmid can be obtained.

After removing the master template by Dpn I enzyme digestion, the mutant plasmid was transformed into E. coli cells, plated in LB culture dishes containing 100 μg/ml ampicillin, and incubated overnight at 37° C.

After the site-directed mutants were identified by sequencing, the expression of ketoreductase was incubated at 25° C., and induced by 0.2 mM IPTG overnight. Then the crude enzyme was obtained by ultrasonication of cells, which was used to detect the reaction characteristics.

According to the reaction characteristic verification, the sites capable of improving the catalytic characteristic of the ketoreductase are from: G6, A94, S96, G117, E144, N156, P193, A205, I224, S176, D85 and R108.

In particular, single point mutations that increase the catalytic selectivity of ketoreductase include: G6S, A94S, A94T, A94N/P/R/M, S96P, G117S, E144S, N156T, N156C, N156S, N156V/G/F, P193G, A205Q, I224V. While S96P, S176P, D85E, R108H can improve the stability of ketone reductase.

Through the computer simulation analysis of the three-dimensional structure of ketoreductase by using software, it was found that A94S/T/N/P/R/M, E144S, N156T/C/S/V/G/F, N156C are located near the center of the enzyme catalysis, which may be related to the low free energy of the binding configuration of the transition state of the desired conformation. S96P and S176P may be related to the reduction of the flexibility of the protein peptide chain.

The saturation mutation is a method for obtaining mutants in which amino acids of a target site are respectively replaced by 19 other amino acids in a short time by modifying a gene encoding a target protein. The method is not only a powerful tool for targeted modification of proteins, but also an important means for studying the structure-function relationship of proteins. Saturation mutations tend to result in more desirable evolutions than single point mutations. However, for these problems that cannot be solved by site directed mutagenesis method, it is precisely the unique feature that the saturation mutation method has.

At present, NNK or NNS degenerate primers are commonly used as primers for saturation mutation. NNK/S will produce 32 possible codons, encoding 20 amino acids and one terminator codon. While, NDT produces 12 possible codons, VHG corresponds to 9 codons, these two degenerate primers plus TGG correspond to 22 codons, no terminator codon, can encode 20 kinds of AA. Compared with NNK/S degenerate primers, the sample size needed to obtain a mutant library covering all amino acids by using three NDT, VHG, TGG degenerate primers for saturation mutation is greatly reduced, which can effectively reduce the screening work.

Based on the study of single point mutation, double point saturation mutation was carried out, which may result in incomparable effect of single point mutation. Double point saturation mutations at positions A94 and N156 were performed in E144S mutant. Saturation mutation primers at both A94 and N156 site used degenerate primers (NDT, VHG, TGG), the mixed mode of the three primers was 12:9:1, which was used for double point saturation mutagenesis. After that, the mutant gene library containing 2-point mutation was amplified by overlap extension PCR, digested by 2-terminal restriction endonuclease Ndel and Xhol enzyme, recovered and ligated into expression vector such as pET22b, transformed into E. coli cells, plated in LB culture dish containing 100 μg/ml ampicillin, cultured overnight at 37° C., and the double point mutant library was obtained, the mutants with selective improvement were obtained by directional screening, including E144S+A94N+N156V, E144S+A94N+N156G, E144S+A94P+N156T, E144S+A94R+N156C and E144S+A94M+N156F.

The catalytic property of the single-point mutant is improved compared with that of the female parent, but the optimal effect is not achieved, and the combination of the mutation points can obtain a better mutant. And carrying out any combination on the mutations to obtain the combined mutant bacteria.

Specifically, comprising the following combination: E144S+S96P, E144S+A94T/S, E144S+N156T/S/C/V/G/F, E144S+G117S, E144S+G6S, E144S+A205Q, E144S+I224V, E144S+S176P, E144S+D85E, E144S+R108H, A94T/S/N/P/R/M+S96P+E144S, E144S+A94T/S/N/P/R/

M+N156T/S/C/V/G/F, E144S+A94T/S/N/P/R/M+N156T/S/C/V/G/F+S96P, E144S+A94T/S+P193G, E144S+A94T/S/N/P/R/M+N156T/S/C/V/G/F+G6S, E144S+A94T/S+G6S, E144S+A94T/S/N/P/R/M+N156T/S/C/V/G/F+G6S+S96P, E144S+A94T/S/N/P/R/M+N156T/S/C/V/G/F+G6S+S96P+R108H and E144S+A94T/S/N/P/R/M+N156T/S/C/V/G/F+G6S+S96P+P193G+R108H, but not limited thereto. Wherein, "/" means "or".

The construction method of the double-point mutation in the combined mutation is the same as the construction method of the single-point mutation, and the whole plasmid PCR method is adopted for construction. Multi-point mutation of three or more mutation sites was amplified by overlap extension PCR to obtain mutant gene containing multi-point mutation. The mutant gene was digested by 2-terminal restriction endonuclease NdeI and XhoI enzyme, recovered and ligated into expression vector such as pET22b, transformed into E. coli cells, plated in LB culture dishes containing 100 μg/ml ampicillin, and cultured overnight at 37° C. to obtain combined mutant. sequencing and identifying.

The overlap extension PCR technique uses primers with complementary ends to form a small overlapping strand of PCR products, and then overlapping and splicing the amplified fragments from different sources by extending the overlapping strand in a subsequent amplification reaction. A multi-point mutant strain is constructed by an overlap extension method, a plurality of sites can be added at one time, the method is time-saving and effective, and the method specifically comprises the following six steps of: preparing a template plasmid and a primer in the first step, obtaining a small fragment in the second step, extending the small fragment to obtain an intermediate fragment in the third step, obtaining a full-length fragment containing all mutation sites in the fourth step, cloning into a vector in the fifth step, and carrying out monoclonal identification and sequencing in the sixth step.

Carrying out shake flask induction expression on the ketoreductase mutant with correct sequence, and the method is: after inoculation into 500 ml of LB liquid medium containing 100 μg/ml ampicillin, the mutant was incubated with shaking at 37° C. until OD600=0.6, IPTG was added to a final concentration of 0.2 mM, and expression was induced at 25° C. After 16 h of induction, the thallus was collected by centrifugation at 6000 g for 10 min. The thallus was disrupted with an ultrasonic cell disruptor, at 4° C., centrifuged at 10000 g for 20 min to obtain supernatant, and the reaction was detected.

According to a typical exemplary embodiment of the present disclosure, a ketoreductase mutant is provided. The amino acid sequence of the ketoreductase mutant is an amino acid sequence has more than 80% homology with the amino acid sequence shown in SEQ ID NO: 1, wherein the mutation at least contains one of the following mutation sites: positions 6, 94, 96, 117, 144, 156, 193, 205, 224, 176, 85 and 108, and glycine at position 6 is mutated to serine; alanine at position 94 is mutated to serine or threonine; serine at position 96 is mutated to proline, asparagine, arginine or methionine; glycine at position 117 is mutated to serine; glutamic acid at position 144 is mutated to serine, asparagine at position 156 is mutated to threonine, cysteine, serine, valine, glycine or phenylalanine, proline at position 193 is mutated to glycine, alanine at position 205 is mutated to glutamine, isoleucine at position 224 is mutated to valine, serine at position 96 is mutated to proline and serine at position 176 is mutated to proline, aspartic acid at position 85 is mutated to glutamic acid and arginine at position 108 is mutated to histidine.

Preferably, the ketoreductase mutant has more than 95%, preferably 96%, more preferably 97%, 98%, 99% or 100% of homology with the amino acid sequences shown in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43.

As used herein, the term "homology" has the meaning commonly known in the art, and the rules and criteria for determining homology between different sequences are also well known to those skilled in the art. The sequences defined by different degrees of homology in the disclosure must also have improved ketoreductase activity at the same time. In the above embodiments, the amino acid sequence of the preferable ketoreductase mutant has more than 95% homology with SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42 or SEQ ID NO:43 and has or encodes an amino acid sequence with improved ketone reductase activity. Such variant sequences may be obtained by those skilled in the art in light of the present disclosure.

The disclosure evolves the wild ketoreductase acCR by means of protein engineering, and obtains the engineered ketoreductase with highly improved enzymatic performance, and the stability of these ketoreductase mutants is significantly improved, especially for acetone and isopropanol, so that in the preparation of chiral hydroxyl heterocyclic substances, there is no need to add glucose/glucose dehydrogenase and formate/formate dehydrogenase, or other coenzymes, the regeneration of cofactors can be completed by adding only isopropanol, which simplifies the composition of the reaction system and reduces the cost. In addition, the ketoreductase mutant disclosed by the disclosure has high stereoselectivity, can be used for preparing chiral alcohol with nearly single purity, so that the utilization rate of a substrate is increased, the post-treatment steps are reduced, and the application value of industrial production of the ketoreductase mutant is improved. According to a typical exemplary embodiment of the present disclosure, a DNA molecule is provided. The DNA molecule encodes the ketoreductase mutants described above. Preferably, the sequence of the DNA molecule has more than 95%, preferably 96% homology, and preferably a sequence of 97%, 98%, 99% or 100% homology with the sequence shown in SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85 or SEQ ID NO: 86.

The above DNA molecules of the present disclosure may also exist in the form of "expression cassette". "Expression cassette" refers to a linear or circular nucleic acid molecule that encompasses DNA and RNA sequences capable of directing the expression of a particular nucleotide sequence in an appropriate host cell. Generally, it includes a promoter operably linked to a target nucleotide, optionally operably linked to a termination signal and/or other regulatory elements. The expression cassette may also include sequences required for correct translation of nucleotide sequences. The coding region usually encodes the target protein, but it also encodes the target functional RNA, such as antisense RNA or untranslated RNA, in the sense or antisense direction. An expression cassette containing a target polynucleotide sequence may be chimeric, meaning that at least one of the components is heterologous to at least one of the other components. The expression cassette can also exist naturally, but can be obtained by effective recombination for heterologous expression.

According to an exemplary embodiment of the present disclosure, a recombinant plasmid is provided. The recombinant plasmid contains any of the DNA molecules described above. The DNA molecule in the recombinant plasmid is placed in position on the recombinant plasmid so that the DNA molecule can be correctly and smoothly replicated, transcribed or expressed.

Although the term "contain" is used herein to define a DNA molecule as defined above, it does not mean that additional sequences not functionally related thereto may be added at either end of the DNA sequence. Those skilled in the art know that, in order to meet the requirements of the recombination operation, it is necessary to add appropriate restriction sites of restriction endonuclease at both ends of the DNA sequence, or to additionally add start codon, terminator codon and the like, and therefore, these situations will not be truly covered if the closed expression is used to define them.

The term "plasmid" used in the disclosure includes any plasmid, cosmid, bacteriophage or *agrobacterium* binary nucleic acid molecule in double-stranded or single-stranded linear or circular form, which is preferably a recombinant expression plasmid, either prokaryotic expression plasmid or eukaryotic expression plasmid, but preferably prokaryotic expression plasmids. In some embodiments, the recombinant plasmids are selected from pET-22b(+), pET-3a(+), pET-3d(+), pET-11a(+), pET-12a(+), pET-14b(+), pET-15b (+), pET-16b(+), pET-17b(+), pET-19b(+), pET-20b(+), pET-21a(+), pET-23a(+), pET-23b(+), pET-24a(+), pET-25b (+), pET-26b(+), pET-27b(+), pET-28a(+), pET-29a(+), pET-30a(+), pET-31b(+), pET-32a(+), pET-35b(+), pET-38b (+), pET-39b(+), pET-40b(+), pET-41a(+), pET-41b(+), pET-42a(+), pET-43a(+), pET-43b(+), pET-44a(+), pET-49b (+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the recombinant plasmid is pET-22b (+).

According to an exemplary embodiment of the present disclosure, a host cell containing any of the recombinant plasmids described above is provided. Host cells suitable for use in the present disclosure include, but are not limited to, prokaryotic, yeast or eukaryotic cells. Preferably, the prokaryotic cell is a *eubacterium*, such as a Gram-negative or Gram-positive bacterium. More preferably, the prokaryotic cell is an *E. coli* BL21 cell or an *E. coli* DH5α competent cell.

According to a typical embodiment of the present disclosure, a method for producing an R-3-hydroxy heterocyclic compound is provided. The method comprises the steps of catalytic reduction of a ketone compound by ketone reductase, wherein the ketone reductase is a ketoreductase mutant of any one above.

The disclosure evolves the wild ketoreductase acCR by means of protein engineering, and obtains the engineered ketoreductase with highly improved enzymatic performance, and the stability of these ketoreductase mutants is significantly improved, especially for acetone and isopropanol, so that in the preparation of chiral hydroxyl heterocyclic substances, there is not need to add glucose/glucose dehydrogenase and formate/formate dehydrogenase, or other coenzymes, the regeneration of cofactors can be completed by adding only isopropanol, which simplifies the composition of the reaction system and reduces the cost. In addition, the ketoreductase mutant disclosed by the disclosure has high stereoselectivity, can be used for preparing chiral alcohol with nearly single purity, so that the utilization rate of a substrate is increased, the post-treatment steps are reduced, and the application value of industrial production of the ketoreductase mutant is improved.

According to a typical embodiment of the present disclosure, the ketone compound is

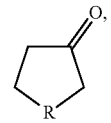

and the product of the reduction reaction is

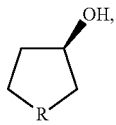

wherein R is selected from O or S atom. Wherein, the conversion rate of R-3-hydroxytetrahydrofuran is >99% with an ee value is 99.6%; the conversion rate of R-3-hydroxytetrahydrothiophene is >99% with an ee value of 99.8%.

According to a typical embodiment of the present disclosure, the ketoreductase is a solution, lyophilized powder, immobilized enzyme or immobilized cell of the ketoreductase mutant.

Preferably, the reaction system of the catalytic reduction reaction includes cofactors such as NAD/NADH and/or NADP/NADPH, cofactor circulatory system including glucose and glucose dehydrogenase, formate and formate dehydrogenase, glucose 6-phosphate and glucose-6-phosphate dehydrogenase, or secondary alcohol and secondary alcohol dehydrogenase. More preferably, the cofactor is isopropanol and no other coenzymes are added.

Preferably, the amount of ketoreductase in the catalytic reduction reaction system is 5 mg-0.1 g crude enzyme lyophilized powder. The dosage of the enzyme in the disclosure is far lower than the dosage of the enzyme in the prior art, and the production cost is reduced.

Preferably, the temperature of the catalytic reduction reaction is 10-37° C., preferably 15-35° C.; the time of the catalytic reduction reaction is 3-48 h, more preferably 6-16 h; the catalytic reduction is carried out at a pH of 6.0-9.5, preferably at a pH of 7.0-7.5. Under the reaction condition, the catalytic performance of the enzyme can be better exerted.

The beneficial effects of the present disclosure will be further illustrated by the following examples.

Example 1: Comparison of Reaction Characteristics for the Preparation of R-3-Hydroxytetrahydrothiophene by Site-Directed Mutagenesis, Saturation Mutagenesis and Combination Mutagenesis of Ketoreductase In a reaction tube of 5 mL, adding 40 mg 3-keto tetrahydrothiophene into 60 ul isopropanol, well mixing and adjusting the pH to 7.0-7.3, adding 0.4 mg NAD, 0.4 mg-4 mg ketoreductase No. 1-44 crude enzyme lyophilized powder and 0.1 M phosphate buffer, the total reaction volume was 0.4 ml, the system pH was 7.0-7.3, stirring and reacting at constant temperature of 30° C.±3° C. If the stability of the ketoreductase is detected, an additional high concentration of isopropyl alcohol is added to the system to carry out the reaction. After 16 h, taking the system and extracting with methyl t-butyl ether, analyzing the organic phase by GC, and the reaction characteristics of mutants with improved catalytic properties in Table 1 were as follows:

TABLE 1

| Sequence number | Mutation site | ee value | Stability |
|---|---|---|---|
| 1 | N/A | 1 | 1 |
| 2 | N156S | ++ | 1 |
| 3 | S96P | + | + |
| 4 | G117S | + | 1 |
| 5 | G6S | ++ | 1 |
| 6 | E144S | +++ | 1 |
| 7 | A94T | ++ | 1 |
| 8 | A94S | +++ | 1 |
| 9 | N156C | ++ | 1 |
| 10 | N156T | ++ | 1 |
| 11 | P193G | ++ | 1 |
| 12 | A205Q | ++ | 1 |
| 13 | I224V | ++ | 1 |
| 14 | S176P | 1 | + |
| 15 | D85E | 1 | + |
| 16 | R108H | 1 | + |
| 17 | E144S + S96P | +++ | + |
| 18 | E144S + A94S | ++++ | 1 |
| 19 | E144S + A94T | ++++ | 1 |
| 20 | E144S + G117S | ++ | 1 |
| 21 | E144S + G6S | +++ | 1 |
| 22 | E144S + A205Q | ++ | 1 |
| 23 | E144S + I224V | +++ | 1 |
| 24 | E144S + S176P | ++ | + |
| 25 | E144S + N156C | ++++ | 1 |
| 26 | A94S + S96P + E144S | ++++ | + |
| 27 | E144S + D85E | +++ | + |
| 28 | E144S + R108H | +++ | + |
| 29 | E144S + N156S | ++++ | 1 |
| 30 | E144S + N156T | ++++ | 1 |
| 31 | E144S + A94T + P193G | ++++ | 1 |
| 32 | E144S + A94T + N156T | ++++ | ++ |
| 33 | E144S + A94S + G6S | ++++ | 1 |
| 34 | E144S + A94M + N156F | ++++ | 1 |
| 35 | E144S + A94N + N156V | +++++ | + |
| 36 | E144S + A94N + N156G | +++++ | 1 |
| 37 | E144S + A94P + N156T | ++++ | 1 |
| 38 | E144S + A94R + N156C | +++++ | 1 |
| 39 | E144S + A94T + N156T + G6S | ++++ | 1 |
| 40 | E144S + A94N + N156V + S96P | +++++ | + |
| 41 | E144S + A94T + N156T + G6S + S96P | +++++ | + |
| 42 | E144S + A94T + N156T + G6S + S96P + R108H | +++++ | ++ |
| 43 | E144S + A94N + N156V + G6S + S96P + P193G + R108H | +++++ | ++ |

Note:
In the enantioselectivity (ee value) column in Table 1
1: represents R enantiomer 50.0-55.99% ee;
+ represents R enantiomer 56.0-74.99% ee;
++: represents R enantiomer 74.99-89.99% ee;
+++: represents R enantiomer 90.0-95.99% ee;
++++: represents R enantiomer 96.0-99.00% ee;
+++++: represents R enantiomer 99.01-100% ee;

In the stability column in the table: 1 represents stability comparable to that of the wild-type ketoreductase; + represents the improvement of stability, and ++ represents the significant improvement of stability.

Example 2: Use of Ketoreductase Mutant in Synthesis of R-3-Hydroxytetrahydrothiophene Chemical reaction for the synthesis of R-3-hydroxytetrahydrothiophene catalyzed by ketoreductase, the following experiment was carried out: adopting 10 ml reaction solution, adding 1 g 3-ketotetrahydrothiophene into 1.5 ml isopropanol, well mixing, adjusting the pH to 7.0-7.3, dropwise adding 7.68 ml 0.1 M phosphate buffer solution of pH7.0 containing 0.01 NAD, 0.005-0.1 g ketoreductase acCR crude enzyme lyophilized powder, the pH of the system was 7.0-7.3, stirring at constant temperature of 30° C.±3° C. for 16 h. Extracting the system with methyl t-butyl ether and detecting the conversion rate and ee value of the organic phase by GC. The specific results are shown in Table 2.

phosphate buffer solution, adding 0.01 g of NAD is added, dropwise adding the substrate mixed solution into the enzyme solution, the system pH was 7.0-7.3, and stirring at constant temperature of 30° C.±3° C. for 40 h. Extracting the system with methyl t-butyl ether and analyzing the organic phase by GC, the ketoreductase mutant of SEQ ID NO: 32 had a conversion rate of 99.3 and an ee value of 98.7%. However, most of the wild-type ketoreductase SEQ ID NO: 1 was denatured in the high concentration isopropanol reaction system, and the reaction results were very poor.

Example 4: Comparison of Reaction Characteristics for the Preparation of R-3-Hydroxytetrahydrothiophene by Partial Ketoreductase Mutants In a reaction tube of 5 mL, adding 0.1 g 3-keto tetrahydrofuran into 150 ul isopropanol, well mixing and adjusting the pH to 7.0-7.3, adding 1 mg NAD, 0.02 g ketoreductase lyophilized powder and 0.1 M phosphate buffer, the total

TABLE 2

| sequence number | Mutation site | 16 h | ee value | Dry powder dosage |
|---|---|---|---|---|
| 1 | N/A (wild type) | 99.1% | 55.1% | 0.1 g |
| 3 | S96P | 99.77% | 60.31% | 0.1 g |
| 9 | N156C | 99.5% | 85.2% | 0.1 g |
| 10 | N156T | 98.81% | 80.41% | 0.1 g |
| 11 | P193G | 100% | 85% | 0.1 g |
| 18 | E144S + A94S | 97.5% | 98.4% | 0.005 g |
| 19 | E144S + A94T | 98% | 97.7% | 0.005 g |
| 25 | E144S + N156C | 99.5% | 97.4% | 0.05 g |
| 32 | E144S + A94T + N156T | 98.7% | 99.0% | 0.03 g |
| 35 | E144S + A94N + N156V | 97.8% | 99.4% | 0.06 g |
| 36 | E144S + A94N + N156G | 98.1% | 99.4% | 0.079 |
| 39 | E144S + A94T + N156T + G6S | 97.8% | 98.9% | 0.05 g |
| 42 | E144S + A94T + N156T + G6S + S96P + R108H | 99.8% | 99.4% | 0.05 g |
| 43 | E144S + A94N + N156V + G6S + S96P + P193G + R108H | 99.8% | 99.7% | 0.05 g |

Example 3

In 10 ml reaction solution, there were 1 g 3-ketotetrahydrothiophene, isopropanol with the final concentration of 60%, ketoreductase lyophilized powder with the mass of 0.025 g, preparing crude enzyme solution by using 0.1M reaction volume was 2 ml, the system pH was 7.0-7.3, stirring at constant temperature of 30° C.±3° C. for 16 h. Extracting the system with methyl t-butyl ether and analyzing the conversion rate and ee value of the organic phase by GC. The reaction characteristics of some of the mutants in Table 1 for 3-ketotetrahydrofuran were as follows (Table 3):

TABLE 3

| sequence | Mutation site | Conversion rate after 16 h | ee value | Dry powder dosage |
|---|---|---|---|---|
| 1 | N/A (wild type) | >99% | 1 | 0.02 g |
| 2 | N156S | >99% | ++ | 0.02 g |
| 5 | G6S | >97% | + | 0.02 g |
| 6 | E144S | >99% | ++ | 0.02 g |
| 7 | A94T | >99% | ++ | 0.02 g |
| 9 | N156C | >99% | +++ | 0.02 g |
| 11 | P193G | >99% | ++ | 0.02 g |
| 12 | A205Q | >99% | ++ | 0.02 g |
| 13 | I224V | >98% | ++ | 0.02 g |
| 17 | E144S + S96P | >98% | +++ | 0.02 g |
| 18 | E144S + A94S | >99% | ++++ | 0.02 g |
| 19 | E144S + A94T | >99% | ++++ | 0.02 g |
| 26 | A94S + S96P + E144S | >99% | +++ | 0.02 g |
| 29 | E144S + N156S | >99% | ++++ | 0.02 g |

TABLE 3-continued

| sequence | Mutation site | Conversion rate after 16 h | ee value | Dry powder dosage |
|---|---|---|---|---|
| 30 | E144S + N156T | >98% | ++++ | 0.02 g |
| 31 | E144S + A94T + P193G | >99% | ++++ | 0.02 g |
| 32 | E144S + A94T + N156T | >99% | ++++ | 0.02 g |
| 34 | E144S + A94M + N156F | >99% | ++++ | 0.02 g |
| 36 | E144S + A94N + N156G | >98% | ++++ | 0.02 g |
| 39 | E144S + A94T + N156T + G6S | >98% | ++++ | 0.02 g |
| 41 | E144S + A94T + N156T + G6S + S96P | >99% | ++++ | 0.02 g |
| 42 | E144S + A94T + N156T + G6S + S96P + R108H | >99% | ++++ | 0.02 g |
| 43 | E144S + A94N + N156V + G6S + S96P + P193G + R108H | >98% | ++++ | 0.02 g |

Note:
In the enantioselectivity column in Table 3
1: represents R enantiomer 50.0-55.99% ee
+ represents R enantiomer 56.0-69.99% ee
++: represents R enantiomer 70.0-89.99% ee
+++: represents R enantiomer 90.0-95.99% ee
+++++: represents R enantiomer 96.0-100% ee

Example 5 preparation of R-3-hydroxytetrahydrofuran by ketoreductase mutants. In 10 mL reaction solution, adding 1 g 3-keto tetrahydrofuran into 1.5 ml isopropanol, well mixing and adjusting the pH to 7.0-7.3, dropwise adding to contain 0.01 g NAD, dissolving 0.05-0.1 g SEQ39 ketoreductase dry powder with 0.1 M phosphate buffer, the system pH was 7.0-7.3, stirring at constant temperature of 30° C.±3° C. for 24 h. Extracting the system with methyl t-butyl ether and analyzing the organic phase by GC, the result showed that the ee value was 99.6% and the conversion rate was greater than 98%.

Example 6: Optimization of the Reaction for Preparing R-3-Hydroxytetrahydrothiophene by Ketoreductase 1. Reaction Temperature:
In a reaction tube of 5 mL, adding 0.1 g 3-keto tetrahydrothiophene into 150 ul isopropanol, well mixing and adjusting the pH to 7.0-7.3, adding 1 mg NAD, 0.005 g SEQ ID NO:18 ketoreductase dry powder and 0.62 ml 0.1 M phosphate buffer, the total reaction volume was 1 ml, the system pH was 7.0-7.3, stirring at constant temperature of 30° C.±3° C. for 16 h. Extracting the system with methyl t-butyl ether and analyzing the organic phase by GC. The results are shown in FIG. 1. As the temperature decreases, the stereoselectivity of ketoreductase tends to increase, while the reaction rate begins to slow.

2. Whole Cell Catalysis:
In a reaction tube of 5 mL, adding 0.1 g 3-keto tetrahydrothiophene into 150 ul isopropanol, well mixing and adjusting the pH to 7.0-7.3, adding 1 mg NAD, 0.05 g SEQ ID NO:42 ketoreductase whole cells and dissolving in 0.62 ml 0.1 M phosphate buffer, the total reaction volume was 1 ml, the system pH was 7.0-7.5, stirring at constant temperature of 30° C.±3C for 16 h. Extracting the system with methyl t-butyl ether and analyzing the organic phase by GC, the result showed that the ee value was greater than 99% and the conversion rate was greater than 98%.

Example 7: Application of Ketoreductase in Preparing R-3-Hydroxytetrahydrothiophene Adopting 10 mL reaction solution, adding 1 g 3-keto tetrahydrothiophene into 4 ml isopropanol, well mixing and adjusting the pH to 7.0-7.3, adding 0.01 g NAD, 0.01 g-0.05 g SEQ ID NO:43 ketoreductase crude enzyme lyophilized powder, dissolving with 0.1 M phosphate buffer, the system pH was 7.0-7.3, reacting at 30° C. for 16 h. Extracting the system with methyl t-butyl ether and testing the organic phase by GC, the conversion rate was 99% and the ee value was 99.7%.

Adopting 10 mL reaction solution, adding 1 g 3-keto tetrahydrothiophene into 4 ml isopropanol, well mixing and adjusting the pH to 7.0-7.3, adding 0.01 g NAD, 0.02 g-0.1 g SEQ ID NO:43 ketoreductase crude enzyme lyophilized powder and dissolving in 0.1 M phosphate buffer to prepare crude enzyme solution, the system pH was 7.0-7.3, stirring at constant temperature of 25° C. for 16 h, raising the temperature to 30° C. and continuing the reaction for 7 h to 10 h. Extracting the system with methyl t-butyl ether and detecting the organic phase by GC, the conversion rate was greater than 99% and the ee value was 99.8%.

When the stereoselectivity of the enzyme increases to a certain extent, especially when the ee value of chiral alcohols reaches more than 99%, it is difficult to break through this value, and the effort required to increase the ee value by 0.1% may be several times or even dozens of times as much as before (for example, from 85% to 86%, from 89% to 90%, from 97% to 98%, etc.). The inventors of the present disclosure have obtained unexpected effects through unremitting efforts, and it can be said that a great progress has been made in obtaining chiral alcohols with ee values as high as 99.8% by enzyme catalysis reaction of partial mutants obtained after modification.

Example 8

Comparison of three mutants of the present disclosure in the preparation of R-3-hydroxytetrahydrothiophene, the reaction system contains: 3-keto tetrahydrothiophene 1 g, ketoreductase recombinant crude enzyme dry powder, isopropanol with final concentration of 30%-50% 0.1 M pH 7.0 phosphate buffer. The reaction pH was 7.0-7.5, reacting at 30° C. 3° C. The reaction volumes and amounts of materials used, and the reaction results are shown in Table 4 below:

TABLE 4

| sequence | Reaction volume | Crude enzyme dry powder amount | Reaction time | Amount of isopropyl alcohol | ee value | Conversion rate |
|---|---|---|---|---|---|---|
| 19 | 3 ml | 0.025 g | 48 h | 0.9 ml (30% V/V) | 97.60% | 99.30% |
| 32 | 4 ml | 0.025 g | 48 h | 1.6 ml (40% V/V) | 99.00% | 98.90% |
| 40 | 5 ml | 0.05 g | 24 h | 2.5 ml (50% V/V) | 99.80% | 99.00% |

The reaction volume used in the above reaction is very small, so that the number of reaction batches is reduced, the utilization rate of the reactor is improved, and the amount of post-treatment organic solvents is reduced, which greatly reduces the production cost.

The mutant obtained in the disclosure by evolutionary means reacts at high temperature (such as 30° C., 31° C., 32° C. or higher temperature) to obtain chiral alcohols with ee values as high as 99.8% or even higher, which is superior to the prior art.

From the above description, it can be seen that the above-described embodiment of the present disclosure achieves the following technical effects:

1) The stability of the ketoreductase is remarkably improved in the present disclosure, especially the tolerance to acetone and isopropanol organic solvents, and the ketoreductase mutant can still maintain high catalytic activity under the high-concentration isopropanol environment. In addition, in the preparation of chiral hydroxy heterocyclic substances, the cofactor can be regenerated by only adding isopropanol, the components of the reaction system are simplified, and the cost is reduced.

2) The ketoreductase mutant disclosed by the disclosure has high stereoselectivity, can be used for preparing chiral alcohol with nearly single purity, so that the utilization rate of a substrate is increased, the production post-treatment steps are reduced, and the ee value of the chiral alcohol obtained by catalytic reaction of part of the ketoreductase mutant is as high as 99.8%, which is far superior to the prior art.

3) The dosage of the enzyme in the disclosure is far lower than the dosage of the enzyme in the prior art, and the production cost is reduced.

The above are only preferred embodiments of the present disclosure and are not intended to limit the present disclosure. For those skilled in the art, the present disclosure may have various modifications and changes. Any modification, equivalent replacement, improvement, etc. made within the spirit and principle of the present disclosure should be included in the protection scope of the present disclosure.

What is claimed is:

1. A ketoreductase mutant having at least 80% sequence identity to the amino acid sequence of sequence SEQ ID NO: 1 and having mutation of one or more amino acids of the SEQ ID NO: 1, wherein the mutation of one or more amino acids comprises glutamate at position 144 mutated to serine, and the mutation of one or more amino acids selected from the group consisting of glycine at position 6 mutated to serine; alanine at position 94 mutated to serine or threonine; serine at position 96 mutants into proline, asparagine, arginine, or methionine; glycine at position 117 mutated to serine; asparagine at position 156 mutated to threonine, cysteine, serine, valine, glycine, or phenylalanine; proline at position 193 mutated to glycine; alanine at position 205 mutated to glutamine; isoleucine at position 224 mutated to valine, serine at position 96 mutated to proline, serine at position 176 mutated to proline; aspartic acid at position 85 mutated to glutamate, and arginine at position 108 mutated to histidine, and having ketoreductase activity.

2. The ketoreductase mutant according to claim 1, wherein the amino acid sequence of the ketoreductase mutant is as shown in SEQ ID NO: 6, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42 or SEQ ID NO: 43.

3. A method for production of an R-3-hydroxyl heterocyclic compound, comprising steps of catalytic reduction of a ketone compound by ketone reductase, wherein the ketone reductase is the mutant of ketone reductase according to claim 1.

4. The method according to claim 3, wherein the ketone compound is

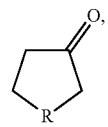

and a product of the reduction reaction is

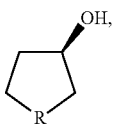

wherein R is selected from O or S atom.

5. The method according to claim 4, wherein conversion rate of R-3-hydroxy tetrahydrofuran is more than 99%, and ee value is 99.6%; conversion rate of R-3-hydroxy tetrahydro-thiophene is more than 99%, and ee value is 99.8%.

6. The method according to claim 3, wherein the ketoreductase is solution, lyophilized powder, immobilized enzyme, or immobilized cell of the mutant of ketone reductase according to claim 1.

7. The method according to claim 3, wherein a reaction system of the catalytic reduction reaction further comprises a cofactor, wherein the cofactor is isopropanol, and no other coenzyme is added.

8. The method according to claim 3, wherein a reaction system of the catalytic reduction reaction further comprises a cofactor, wherein the cofactor is NAD/NADH and/or NADP/NADPH, and a cofactor circulation system comprises glucose and glucose dehydrogenase, formate and formate dehydrogenase, glucose 6-phosphoric acid and glucose-6-phosphate dehydrogenase, or secondary alcohol and secondary alcohol dehydrogenase.

9. The method according to claim 3, wherein addition amount of the ketone reductase in the reaction system of the catalytic reduction reaction is 5 mg~0.1 g lyophilized powder of crude enzyme/1 g substrate.

10. The method according to claim 3, wherein temperature of the catalytic reduction reaction is 10~37° C.

11. The method according to claim 3, wherein time of the catalytic reduction reaction is 3~48 h.

12. The method according to claim 3, wherein the catalytic reduction reaction is carried out under a condition of with—pH 6.0-9.5.

13. The method according to claim 10, wherein temperature of the catalytic reduction reaction is 15~35° C.

14. The method according to claim 11, wherein time of the catalytic reduction reaction is 6~27 h.

* * * * *